(12) United States Patent
Wu

(10) Patent No.: US 6,637,275 B2
(45) Date of Patent: Oct. 28, 2003

(54) UNIFORM PRESSURE TYPE THREE-DIMENSIONAL PRESSURE BEARING SURFACE MEASURING INSTRUMENT STRUCTURE

(75) Inventor: Yao-Ching Wu, Taichung (TW)

(73) Assignee: Aerospace Industrial Development Co., Ltd., Taichung (TW)

( * ) Notice: Subject to any disclaimer, the term of this patent is extended or adjusted under 35 U.S.C. 154(b) by 0 days.

(21) Appl. No.: 10/062,531

(22) Filed: Feb. 5, 2002

(65) Prior Publication Data
US 2002/0178834 A1 Dec. 5, 2002

(30) Foreign Application Priority Data

Jun. 1, 2001 (TW) .................................. 90209242 U
Dec. 4, 2001 (TW) .................................. 90221223 U

(51) Int. Cl.[7] .............................. G01D 7/00; G01L 3/00
(52) U.S. Cl. ................................................. 73/862.046
(58) Field of Search ........................... 73/767, 774, 788, 73/819, 856, 862.041, 862.042, 862.046

(56) References Cited

U.S. PATENT DOCUMENTS 5,430,778 A * 7/1995 Yaginuma .................... 376/258
5,452,689 A * 9/1995 Karlan ........................ 123/56.2
6,231,032 B1 * 5/2001 Ivey, Jr. ......................... 261/26

* cited by examiner

Primary Examiner—Max Noori
(74) Attorney, Agent, or Firm—Rosenberg, Klein & Lee

(57) ABSTRACT

A uniform pressure type three-dimensional pressure bearing surface measuring instrument structure includes a housing, multiple measuring rods, multiple height sensors, multiple connection support cylinders, and multiple connection pipes. The connection support cylinders are connected with the connection pipes which are connected with each other, so that the connection support cylinders and the connection pipes may form a pressure connection system. Thus, the three-dimensional pressure bearing surface measuring instrument structure may be used to the pressure distribution of the user's hip by measuring the height variation of the measuring rods, thereby forming a three-dimensional spatial curve of a constant pressure so as to make a seat cushion of a constant pressure according to the three-dimensional spatial curve, so that the seat cushion may satisfy the ergonomic design.

8 Claims, 5 Drawing Sheets

UNIFORM PRESSURE TYPE THREE-DIMENSIONAL PRESSURE BEARING SURFACE MEASURING INSTRUMENT STRUCTURE

BACKGROUND OF THE INVENTION

1. Field of the Invention

The present invention relates to a uniform pressure type three-dimensional pressure bearing surface measuring instrument structure, and more particularly to a uniform pressure type three-dimensional pressure bearing surface measuring instrument structure that may be used to the pressure distribution of the user's hip by measuring the height variation of the measuring rods, thereby forming a three-dimensional spatial curve of a constant pressure so as to make a seat cushion of a constant pressure according to the three-dimensional spatial curve, so that the seat cushion may satisfy the ergonomic design.

2. Description of the Related Art

A conventional pressure bearing surface measuring instrument in accordance with the prior art may be used to measure the curve of a seat cushion, and comprises multiple measuring rods extended through a foam body. By contact of a person to be measured, the foam body may be deformed to drive the measuring rods to move, thereby forming different height variations, so as to measure the curve of the person to be measured, so that the seat cushion may be made according to the curve of the person to be measured.

However, when the foam body is compressed, the measuring rods are easily displaced during deformation of the foam body, thereby affecting the measuring effect of the three-dimensional curve. In addition, when the foam body is subjected to a larger pressing force at one point to produce a larger deformation, the foam body will produce a larger reaction at that point, so that the pressure at that point is relatively increased, thereby easily causing a stress concentration. Further, the foam body is easily worn out during a long-term utilization and has to be replaced, thereby causing consumption of material. Further, the foam body cannot be replaced easily when being worn out, thereby causing inconvenience in maintenance of the conventional pressure bearing surface measuring instrument.

SUMMARY OF THE INVENTION

The present invention has arisen to mitigate and/or obviate the disadvantage of the conventional pressure bearing surface measuring instrument.

The primary objective of the present invention is to provide a uniform pressure type three-dimensional pressure bearing surface measuring instrument structure that may be used to the pressure distribution of the user's hip by measuring the height variation of the measuring rods, thereby forming a three-dimensional spatial curve of a constant pressure so as to make a seat cushion of a constant pressure according to the three-dimensional spatial curve, so that the seat cushion may satisfy the ergonomic design.

Another objective of the present invention is to provide a uniform pressure type three-dimensional pressure bearing surface measuring instrument structure, wherein by provision of the pressure adjusting nozzle, the pre-pressure in the entire system of the connection support cylinders and the connection pipes may be changed and adjusted previously according to the weight of the person to be measured, so as to fit users of different weights.

In accordance with a first aspect of the present invention, there is provided a uniform pressure type three-dimensional pressure bearing surface measuring instrument structure, comprising:

a housing, multiple measuring rods, multiple height sensors, multiple connection support cylinders, and multiple connection pipes, wherein:

the connection support cylinders are connected with the connection pipes which are connected with each other, so that the connection support cylinders and the connection pipes may form a pressure connection system.

In accordance with a second aspect of the present invention, there is provided a uniform pressure type three-dimensional pressure bearing surface measuring instrument structure, wherein the multiple connection pipes are undefined, and each of the connection support cylinders is replaced by a compression spring which is mounted on the measuring rod, and is biased between a resting member of the measuring rod and a pressure adjusting plate of the pressure adjusting device.

Further benefits and advantages of the present invention will become apparent after a careful reading of the detailed description with appropriate reference to the accompanying drawings.

DETAILED DESCRIPTION OF THE INVENTION

Figure 1:
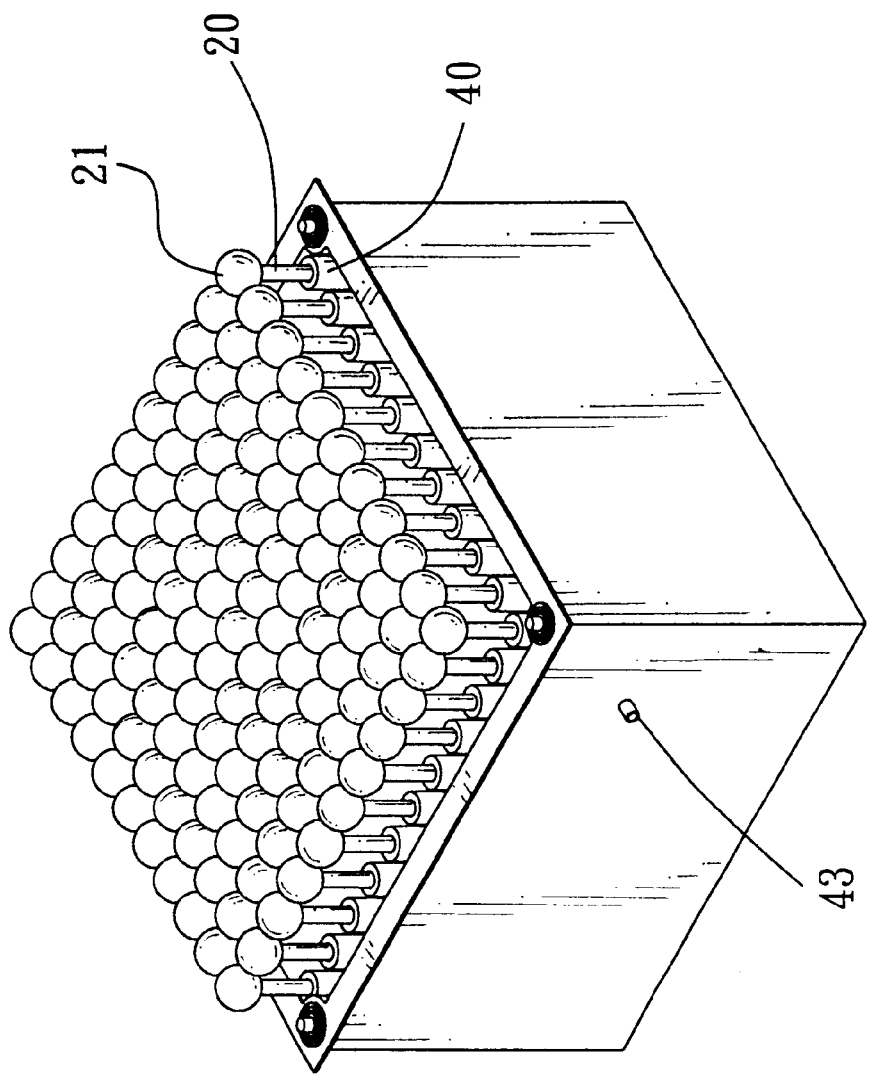
FIG. 1 is a perspective view of a uniform pressure type three-dimensional pressure bearing surface measuring instrument structure in accordance with a first embodiment of the present invention.
Figure 2:
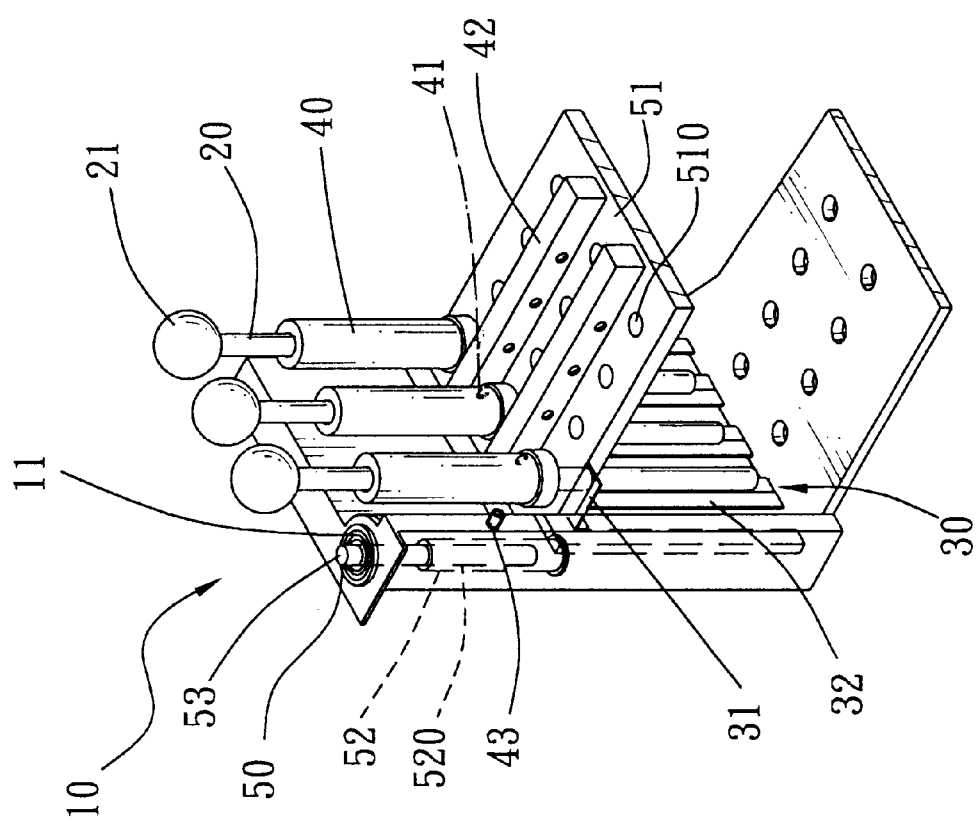
FIG. 2 is a partially cut-away perspective view of the uniform pressure type three-dimensional pressure bearing surface measuring instrument structure as shown in FIG. 1.
Figure 3:
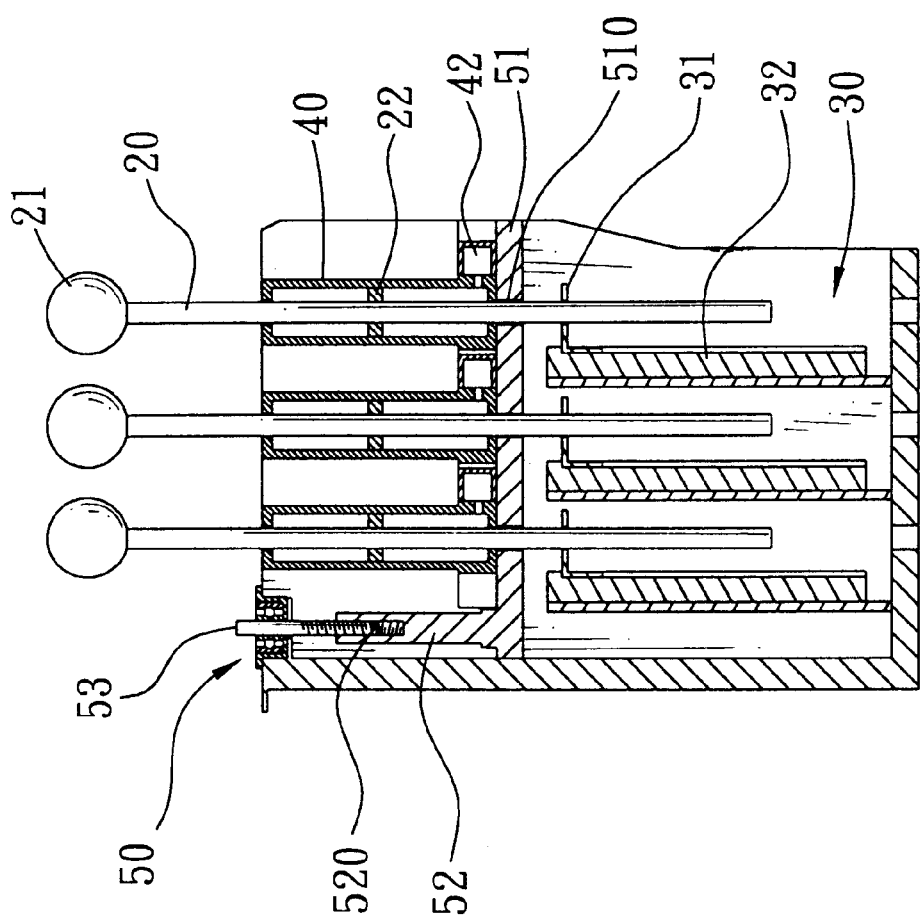
FIG. 3 is a partially cut-away plan cross-sectional view of the uniform pressure type three-dimensional pressure bearing surface measuring instrument structure as shown in FIG. 1.

Referring to the drawings and initially to FIGS. 1–3, a uniform pressure type three-dimensional pressure bearing surface measuring instrument structure in accordance with a first embodiment of the present invention comprises a housing 10, multiple measuring rods 20, multiple height sensors 30, multiple connection support cylinders 40, multiple connection pipes 42, and a pressure adjusting device 50.

The housing 10 is an opening facing upward, and has four corners each provided with a bearing 11 to co-operate with the pressure adjusting device 50.

The pressure adjusting device 50 includes a pressure adjusting plate 51 adjustably mounted in the housing 10 and formed with multiple through holes 510, four adjusting guide posts 52 each secured on the pressure adjusting plate 51, each located on one of the four corners of the housing 10, and each formed with a screw bore 520, and four adjusting bolts 53 each rotatably mounted in the bearing 11 of one of the four corners of the housing 10, and each screwed into the screw bore 520 of one of the four adjusting guide posts 52. Thus, the height of the pressure adjusting plate 51 may be adjusted by rotating the adjusting bolts 53.

Figure 5:
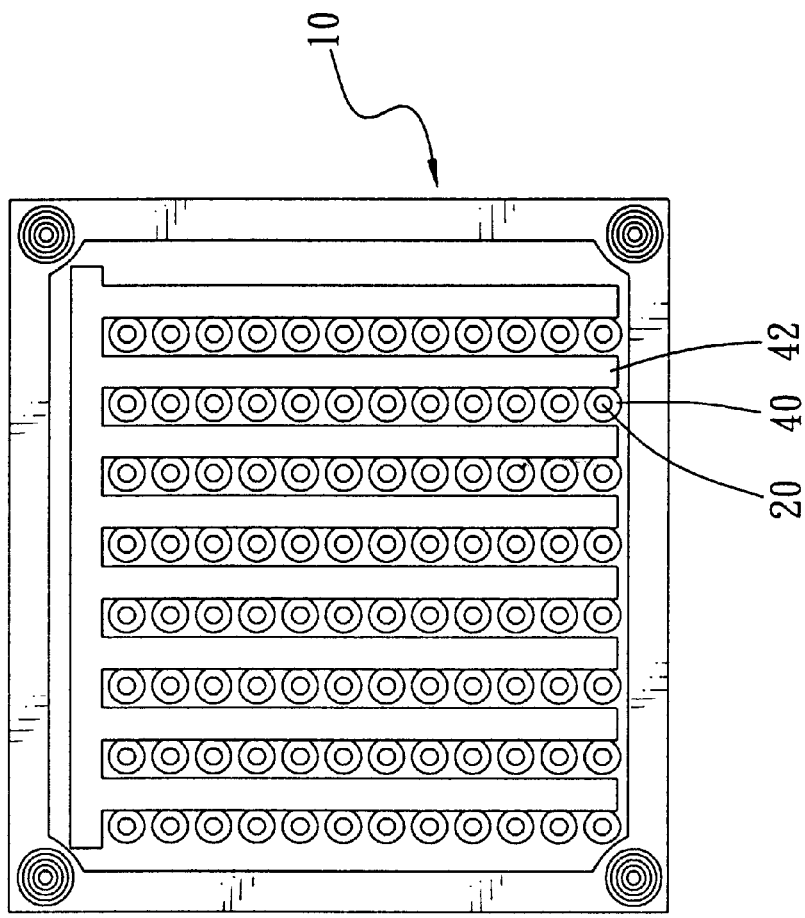
FIG. 5 is a top plan view of the uniform pressure type three-dimensional pressure bearing surface measuring instrument structure as shown in FIG. 1.
Figure 4:
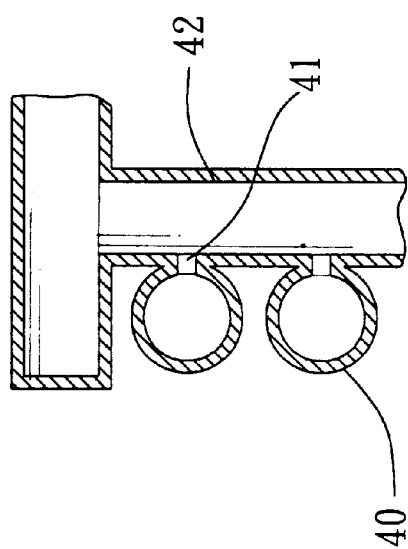
FIG. 4 is a partially cut-away top plan cross-sectional view of the uniform pressure type three-dimensional pressure bearing surface measuring instrument structure as shown in FIG. 2.

Each of the connection pipes 42 is mounted and supported on the pressure adjusting plate 51 of the pressure adjusting device 50. Each of the connection support cylinders 40 is mounted and supported on the pressure adjusting plate 51 of the pressure adjusting device 50, and is connected to one of the connection pipes 42. Each of the connection support cylinders 40 is formed with a lateral hole 41 connected to the connection pipe 42 as shown in FIG. 4, so that the connection support cylinders 40 are connected with the connection pipes 42 which are connected with each other as shown in FIG. 5. Thus, the connection support cylinders 40 and the connection pipes 42 may form a pressure connection system. One of the connection pipes 42 is provided with a pressure adjusting nozzle 43, whereby fluid, such as the air, may be poured into and may be released from the pressure adjusting nozzle 43, so that the entire system of the connection support cylinders 40 and the connection pipes 42 may have different pressures to satisfy the object or the person to be measured.

Each of the measuring rods 20 is slidably mounted in one of the connection support cylinders 40, and has an upper end provided with a ball-shaped resting member 21 that may be in contact with the surface of the object or the person to be measured, and a lower end extended through the one of the through holes 510 of the pressure adjusting plate 51 of the pressure adjusting device 50. Each of the measuring rods 20 is provided with a piston 22 that may be driven by the measuring rod 20 to move in the connection support cylinder 40. Thus, when the height of the measuring rod 20 is changed, the piston 22 may be moved by movement of the measuring rod 20 to compress the fluid, such as air, contained in the connection support cylinder 40, thereby forming a pressure variation.

Each of the height sensors 30 includes a support a post 33 mounted in the housing 1, a circuit board 32 secured on the support post 33, and a connector 31 having a first section movably mounted on the circuit board 32 and a second section secured on the lower end of one of the measuring rods 20 to move therewith. Thus, when one of the measuring rods 20 is moved, the connector 31 may be moved with the lower end of the measuring rod 20 to displace on the circuit board 32, so that the height of the measuring rod 20 may be detected, and the detected height signal may be collected and sent into a trailing processor that may perform a height versus pressure analysis, thereby forming a three-dimensional spatial image.

In operation, when the object or the person to be measured is placed or seated on the measuring rods 20 as shown in FIG. 1, the resting members 21 of the measuring rods 20 may be pressed downward by the weight, and the measuring rods 20 may be moved downward, so that the measuring rods 20 may form various height distributions.

Thus, when each of the measuring rods 20 is moved downward, the connector 31 of each of the height sensors 30 may be moved with the lower end of the measuring rod 20 to displace on the circuit board 32, so that the value of the height of each of the measuring rods 20 may be detected by each of the height sensors 30, and the detected height signal may be collected and sent by the circuit board 32 into a trailing processor that may perform a height versus pressure analysis, so as to transform the height values into pressure values, thereby forming a three-dimensional spatial image that indicates a three-dimensional spatial curve that may be used to make the model of an object, such as a soft seat cushion.

It is appreciated that, when the measuring rods 20 are pressed to move downward, the pistons 22 may be moved by movement of the measuring rods 20 to compress the fluid contained in the connection support cylinders 40, and the connection support cylinders 40 are connected with the connection pipes 42 which are connected with each other, so that the entire system may instantaneously transmit the pressure to form a constant pressure state.

Thus, all of the points of the three-dimensional spatial curve measured by the three-dimensional pressure bearing surface measuring instrument structure of the present invention are located at the constant pressure lines, so that the three-dimensional spatial curve presents a three-dimensional constant pressure variation.

Thus, all of the points of the seat cushion made by the model simulated by the three-dimensional spatial curve measured by the three-dimensional pressure bearing surface measuring instrument structure of the present invention may co-operate to form a constant pressure state, so that the pressure may be distributed on the seat cushion evenly and smoothly, thereby preventing from incurring a stress concentration.

Thus, when the user is seated on the seat cushion, he is subjected to a constant pressure, thereby providing a comfortable sensation to the user. Thus, the soft seat cushion made by the three-dimensional spatial simulation of the uniform pressure type three-dimensional pressure bearing surface measuring instrument structure in accordance with the present invention is especially available for the handicapped people who is always seated on the wheelchair.

In addition, by provision of the pressure adjusting nozzle 43, the pre-pressure in the entire system of the connection support cylinders 40 and the connection pipes 42 may be changed and adjusted previously according to the weight of the person to be measured, so as to fit users of different weights.

Accordingly, the uniform pressure type three-dimensional pressure bearing surface measuring instrument structure in accordance with the present invention may be used to the pressure distribution of the user's hip by measuring the height variation of the measuring rods 20, thereby forming a three-dimensional spatial curve of a constant pressure so as to make a seat cushion of a constant pressure according to the three-dimensional spatial curve, so that the seat cushion may satisfy the ergonomic design.

Figure 6:
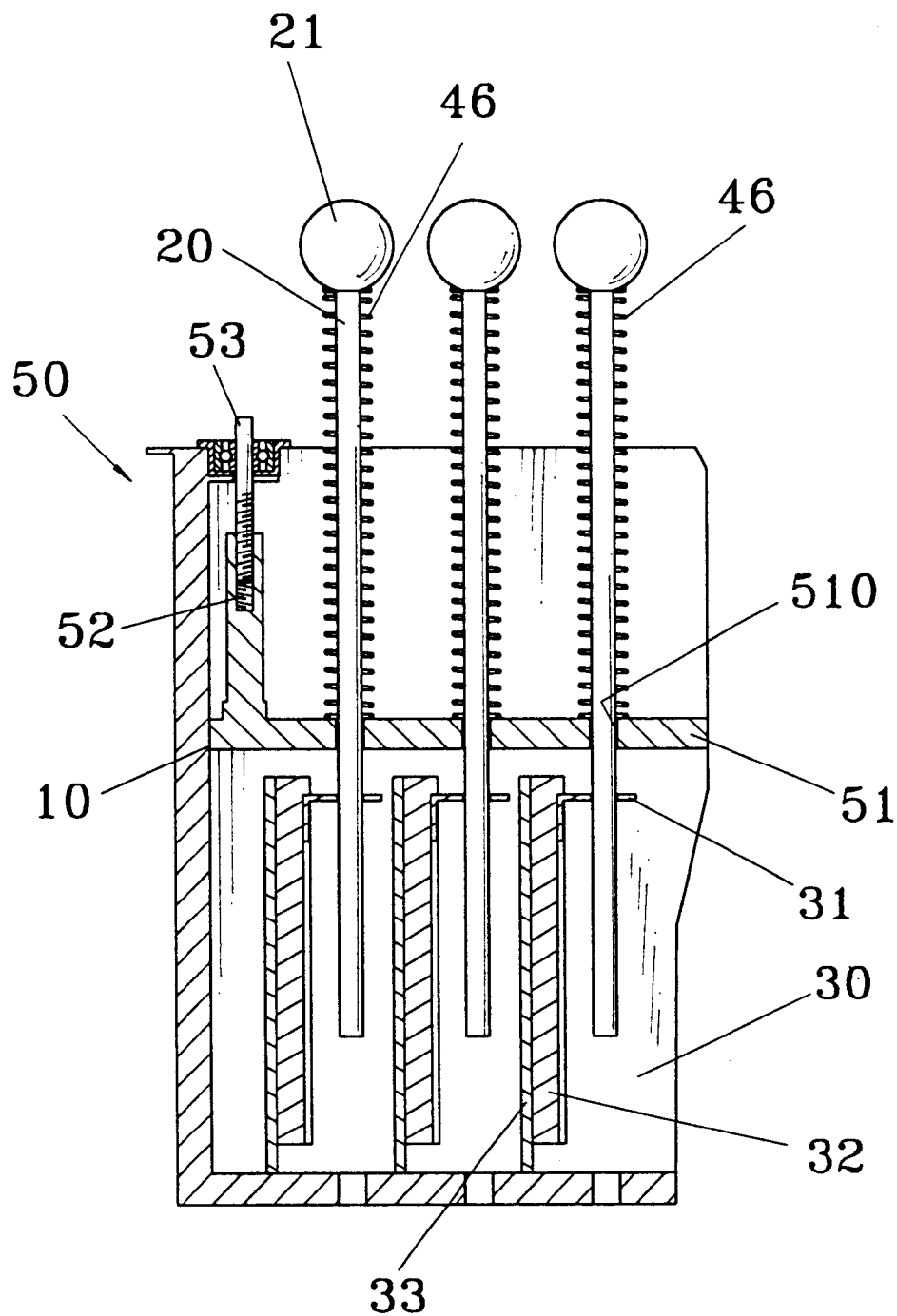
FIG. 6 is a partially cut-away plan cross-sectional view of a uniform pressure type three-dimensional pressure bearing surface measuring instrument structure in accordance with a second embodiment of the present invention.

Referring to FIG. 6, a uniform pressure type three-dimensional pressure bearing surface measuring instrument structure in accordance with a second embodiment of the present invention is shown.

The multiple connection pipes 42 are undefined, and each of the connection support cylinders 40 is replaced by a compression spring 46 which is mounted on the measuring rod 20, and is biased between the resting member 21 and the pressure adjusting plate 51 of the pressure adjusting device 50.

Although the invention has been explained in relation to its preferred embodiment as mentioned above, it is to be understood that many other possible modifications and variations can be made without departing from the scope of the present invention. It is, therefore, contemplated that the appended claim or claims will cover such modifications and variations that fall within the true scope of the invention.

What is claimed is:

1. A uniform pressure type three-dimensional pressure bearing surface measuring instrument structure, comprising:
   a housing;
   a plurality of measuring rods received within said housing and each said measuring rod having a piston mounted thereon;
   a plurality of height sensors mounted on said housing, each said height sensor corresponding to a respective one of said measuring rods, each said height sensor measuring displacement of said respective measuring rod; and,
   a plurality of connection support cylinders, each said connection support cylinder receiving a respective one of said measuring rods, said connection support cylinders being fluidicly connected with one another by a plurality of connection pipes, said connection support cylinders receiving a fluid whereby displacement of said pistons produces fluid flow between said plurality of connection support cylinders.

2. The uniform pressure type three-dimensional pressure bearing surface measuring instrument structure as recited in claim 1, wherein one of the connection pipes is provided with a pressure adjusting nozzle, whereby fluid may be poured into and may be released from the pressure adjusting nozzle, so that the entire system of the connection support cylinders and the connection pipes have different pressures.

3. The uniform pressure type three-dimensional pressure bearing surface measuring instrument structure as recited in claim 1, wherein each of the connection support cylinders is formed with a lateral hole connected to a corresponding connection pipe.

4. The uniform pressure type three-dimensional pressure bearing surface measuring instrument structure as recited in claim 1, wherein each of the measuring rods is slidably mounted in one of the connection support cylinders, and has an upper end provided with a ball-shaped resting member for contacting a surface of an object or a person to be measured.

5. The uniform pressure type three-dimensional pressure bearing surface measuring instrument structure as recited in claim 1, wherein each of the connection support cylinders includes a compression spring which is mounted on the measuring rod, and is biased between a resting member of the measuring rod and a pressure adjusting plate of the pressure adjusting device.

6. The uniform pressure type three-dimensional pressure bearing surface measuring instrument structure as recited in claim 1, wherein each of the height sensors includes a support post mounted in the housing, a circuit board being secured on the support post, and a connector having a first section movably mounted on the circuit board and a second section secured on a lower end of one of the measuring rods to move therewith.

7. The uniform pressure type three-dimensional pressure bearing surface measuring instrument structure as recited in claim 1, wherein the housing has an opening facing upward and has four corners each provided with a bearing to cooperate with a pressure adjusting device, the pressure adjusting device including a pressure adjusting plate adjustably mounted in the housing, four adjusting guide posts each secured on the pressure adjusting plate and each located on one of the four corners of the housing, and each formed with a screw bore, and four adjusting bolts each rotatably mounted in the bearing of one of the four corners of the housing, and each screwed into the screw bore of one of the four adjusting guide posts.

8. The uniform pressure type three-dimensional pressure bearing surface measuring instrument structure as recited in claim 7, wherein the pressure adjusting plate is formed with multiple through holes, and each of the measuring rods has a lower end extended through the one of the through holes of the pressure adjusting plate of the pressure adjusting device.

* * * * *